United States Patent [19]

Bitensky et al.

[11] Patent Number: 5,789,151
[45] Date of Patent: *Aug. 4, 1998

[54] PROLONGED COLD STORAGE OF RED BLOOD CELLS BY OXYGEN REMOVAL AND ADDITIVE USAGE

[75] Inventors: Mark W. Bitensky, Boston; Tatsuro Yoshida, Newton, both of Mass.

[73] Assignee: The Regents of the University of California, Los Alamos, N. Mex.

[ * ] Notice: The term of this patent shall not extend beyond the expiration date of Pat. No. 5,624,794.

[21] Appl. No.: 857,474

[22] Filed: May 15, 1997

[51] Int. Cl.⁶ .................. A01N 1/02; A61M 37/00
[52] U.S. Cl. ........................ 435/2; 604/4
[58] Field of Search ...................... 435/2; 604/4

[56] References Cited

U.S. PATENT DOCUMENTS 4,585,735  4/1986  Meryman et al. ................ 435/2
5,476,764  12/1995  Bitensky ............................. 435/2
5,624,794  4/1997  Bitensky et al. .................... 435/2

*Primary Examiner*—Ponnathapura Achutamurthy
*Assistant Examiner*—Brett L. Nelson
*Attorney, Agent, or Firm*—Samuel M. Freund

[57] ABSTRACT

Prolonged cold storage of red blood cells by oxygen removal and additive usage. A cost-effective, 4° C. storage procedure that preserves red cell quality and prolongs post-transfusion in vivo survival is described. The improved in vivo survival and the preservation of adenosine triphosphate levels, along with reduction in hemolysis and membrane vesicle production of red blood cells stored at 4° C. for prolonged periods of time, is achieved by reducing the oxygen level therein at the time of storage; in particular, by flushing the cells with an inert gas, and storing them in an aqueous solution which includes adenine, dextrose, mannitol, citrate ion, and dihydrogen phosphate ion, but no sodium chloride, in an oxygen-permeable container which is located in an oxygen-free environment containing oxygen-scavenging materials.

21 Claims, 8 Drawing Sheets

PROLONGED COLD STORAGE OF RED BLOOD CELLS BY OXYGEN REMOVAL AND ADDITIVE USAGE

FIELD OF THE INVENTION

The present invention relates generally to the liquid preservation of blood and, more particularly, to the refrigerated storage of red blood cells in the presence of additives and in the absence of oxygen. The invention was made with government support under Contract No. W-7405-ENG-36 awarded by the U.S. Department of Energy to the Regents of The University of California. The government has certain rights in the invention.

BACKGROUND OF THE INVENTION

The current blood supply is considerably smaller than the need therefor. Stored blood is considered unusable after about 6 weeks of steady deterioration in storage as determined by the inability of such cells to survive in the circulation after transfusion, which in part is caused by hemoglobin oxidation and degradation and adenosine triphosphate (ATP) depletion. Moreover, the risks involved in receiving blood from nonautologous donors remain significant. In order to address current needs, blood storage techniques must be simple, inexpensive and long term.

Red blood cells (RBCs) survive for about 4 months under conditions of turbulent flow in the body without protein synthesis. Oxygen ($O_2$) is essential for the conversion of hemoglobin (Hb) to met-Hb, the breakdown of which produces toxic products such as hemichrome, hemin and free $Fe^{3+}$. Together with $O_2$, these products catalyze the formation of hydroxyl radicals (OH●), and both OH● and the met-Hb breakdown products damage the red cell lipid membrane, the membrane skeleton, and the cell contents. As will be discussed hereinbelow, current approaches to red cell preservation do not address the hemoglobin breakdown damage pathway.

Refrigeration reversibly disables the enzymes essential for met-Hb reduction in vivo, increases the solubility of damaging $O_2$ (almost by a factor of two) in the environment of the red blood cells, and permits the level of ATP to decrease by diminishing the glycolytic rate (at 4° C. the rate is about 1% of that found at 37° C.). Reduction of red cell ATP concentration results in echinocyte (an unstable form of red blood cells) formation, increased rates of membrane vesiculation, loss of red cell surface area, and accelerated sequestration by splenic macrophages. Vesiculation continues throughout the cold storage period, is exacerbated by echinocyte formation, and decreases red blood cell survival by decreasing red blood cell membrane area.

The effects of elevation and preservation of ATP levels in blood storage situations has been studied. For example, in "Studies In Red Blood Cell Preservation-7. In Vivo and in Vitro Studies With A Modified Phosphate-Ammonium Additive Solution," by Greenwalt et al., Vox Sang 65, 87–94 (1993), the authors determined that the experimental additive solution (EAS-2) containing in mM: 20 $NH_4Cl$, 30 $Na_2HPO_4$, 2 adenine, 110 dextrose, 55 mannitol, pH 7.15, is useful in extending the storage shelf-life of human RBCs from the current standard of 6 weeks to an improved standard of 8–9 weeks. Packed RBCs are suitable for transfusion following the removal of the supernatant with a single washing step. Greenwalt et al. also conclude that factors other than ATP concentration appear to play an increasingly important role in determining RBC viability after 50 days of storage. They cite the results of L. Wood and E. Beutler in "The Viability Of Human Blood Stored In Phosphate Adenine Media," Transfusion 7, 401–408 (1967), and find in their own experiments that the relationship between ATP concentration and 24h RBC survival measurements appears to become less clear after about 8 weeks of storage. E. Beutler and C. West restate that the relationship between red cell ATP concentration and viability is a weak one after prolonged periods of storage in "Storage Of Red Cell Concentrates In CPD-A2 For 42 and 49 Days," J. Lab. Clin. Med. 102, 53–62 (1983).

U.S. Pat. No. 4,585,735, for "Prolonged Storage Of Red Blood Cells," which issued to Harold T. Meryman et al. on Apr. 29, 1986, discloses a hypotonic suspension medium and a method for prolonged storage of red blood cells at about 4° C. The preferred hypotonic suspending solution contained 110 mM glucose, 55 mM mannitol, 7.9 mM potassium citrate, 25.8 mM potassium phosphate, 14.7 mM potassium dihydrogen phosphate, 2 mM adenine, and 50 mM $NH_4Cl$. It was compared with an isotonic solution containing 110 mM glucose, 55 mM mannitol, 58.6 mM potassium citrate, 25.8 mM potassium phosphate, 14.7 mM potassium dihydrogen phosphate, and 2 mM adenine in a demonstration of 24 h in vivo survival for red cells stored in the two solutions for periods ranging up to 125 days. From FIG. 2 of the '735 patent, it may be observed that the hypotonic solution provides significantly better protection for the red blood cells. Prior to transfusion, the cells were sedimented by centrifugation and resuspended in a transfusable solution.

In "Effects Of Oxygen On Red Cells During Liquid Storage at +4° C.," by Hogman et al., Vox Sang 51, 27–34 (1986), the authors disclose that the red cell content of ATP is slightly better maintained after 2–3 weeks when blood bags prepared by the standard procedures were stored in an oxygen-free atmosphere. Venous blood was refrigerated and deprived of additional oxygen during storage, by placing the moderately oxygen-permeable storage bags (standard polyvinyl chloride (PVC) bags were employed and not the highly permeable bags currently available) in a nitrogen environment and thereby gradually reducing the level of oxygen saturation. The reduction in oxygen concentration occurs slowly during storage at 4° C., and is far from complete, starting at ~60% and reaching ~30% hemoglobin saturation at 5 weeks. No conclusion could be drawn concerning the effects of this procedure on the overall quality of stored cells. These authors did not address or significantly reduce the oxygen-dependent damage to hemoglobin and the oxygen-mediated damage caused by hemoglobin breakdown products.

U.S. Pat. No. 5,624,794 for "Method Using Oxygen Removal For Extending The Useful Shelf-Life Of Refrigerated Red Blood Cells," which issued to Mark W. Bitensky et al. on Apr. 29, 1997, discloses a method, using oxygen removal at the time of storage, for preserving adenosine triphosphate levels and reducing hemolysis and membrane vesicle production in red blood cells stored at 4° C. for prolonged periods of time. To achieve a low oxygen concentration, the red blood cells are flushed with an inert gas and stored in an oxygen gettering environment.

Accordingly, it is an object of the present invention to provide a procedure for blood storage which takes advantage of the positive effects of oxygen removal and of the use of additive solutions for addressing the problems of hemoglobin degradation, red blood cell lysis (hemolysis) and ATP depletion in a manner consistent with the practice of autologous transfusion and enhanced heterologous transfusion logistics, and which achieves significant prolongation of the time during which refrigerated storage of red blood cells is not detrimental to their subsequent use.

Another object of the present invention is to provide a procedure for prolonged blood storage while minimizing the complexity of the procedures required for preparing transfusible samples.

Yet another object of the present invention is to provide a procedure for prolonged blood storage in which use of additive solutions is synergistic with anaerobic storage.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for storing red blood cells hereof includes the steps of: mixing a sample of whole blood containing the red blood cells to be stored with an anticoagulant solution, forming thereby a first suspension of red blood cells, concentrating the red blood cells from the liquid portion (plasma) of the first suspension, forming thereby a mass of packed red blood cells, mixing the packed red blood cells so produced with an additive solution which includes an aqueous solution of adenine, dextrose, mannitol, citrate ion, and dihydrogen phosphate ion, with no sodium chloride, forming thereby a second suspension of red blood cells, reducing the oxygen level of the red blood cells in the second suspension of red blood cells to less than 10% of the level of oxygen therein when obtained by flushing the red blood cells with an inert gas, and storing the red blood cells in the second suspension of red blood cells at 4° C.

Preferably, no further exposure of the cooled red blood cells to oxygen is permitted.

Preferably also, the level of oxygen in the stored red blood cells is reduced during storage.

It is preferred that the amount of additive solution be sufficient to achieve a final hematocrit of between 30% and 60%.

It is also preferred that the pH of the additive solution be adjusted to approximately 7.1.

In another aspect of the present invention, and in accordance with its objects and purposes, the method for storing red blood cells hereof includes the steps of: forming a mass of packed red blood cells, mixing the packed red blood cells with an additive solution which includes an aqueous solution of adenine, dextrose, mannitol, citrate ion, and dihydrogen phosphate ion, with no sodium chloride, forming thereby a suspension of red blood cells, reducing the level of oxygen of the red blood cells in the suspension of red blood cells to less than 10% of the level of oxygen therein when obtained, and storing the red blood cells in the suspension of red blood cells at 4° C.

Preferably, no further exposure of the cooled red blood cells to oxygen is permitted.

Preferably also, the level of oxygen in the stored red blood cells is reduced during storage.

It is preferred that the amount of additive solution be sufficient to achieve a final hematocrit of between 30% and 60%.

It is also preferred that the pH of the additive solution be adjusted to approximately 7.1.

Benefits and advantages of the present invention include the preservation of ATP levels and the reduction of hemolysis and accumulation of membrane vesicles in the refrigerated RBCs, as a consequence of creating an environment ($O_2$ removal) that prevents hemoglobin degradation, with the result that useful refrigerated storage periods may be prolonged.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 1a compares the results from a double labeling procedure, while FIG. 1b compares the results from a single labeling procedure.

FIG. 2a compares anaerobic (black circles) with aerobic (open circles) storage in OFAS1, FIG. 2b comparing aerobic storage in conventional storage media (Xs) with anaerobic storage in OFAS1 (black circles), while FIG. 2c compares aerobic storage in conventional storage media (Xs) with aerobic storage in OFAS1 (open circles). FIG. 2c illustrates that there is a beneficial effect from the use of OFAS1 over conventional storage solutions without oxygen removal, but the effect is much smaller than the combined effects of oxygen removal and OFASI shown in FIG. 2a.

DETAILED DESCRIPTION

Figure 1A:
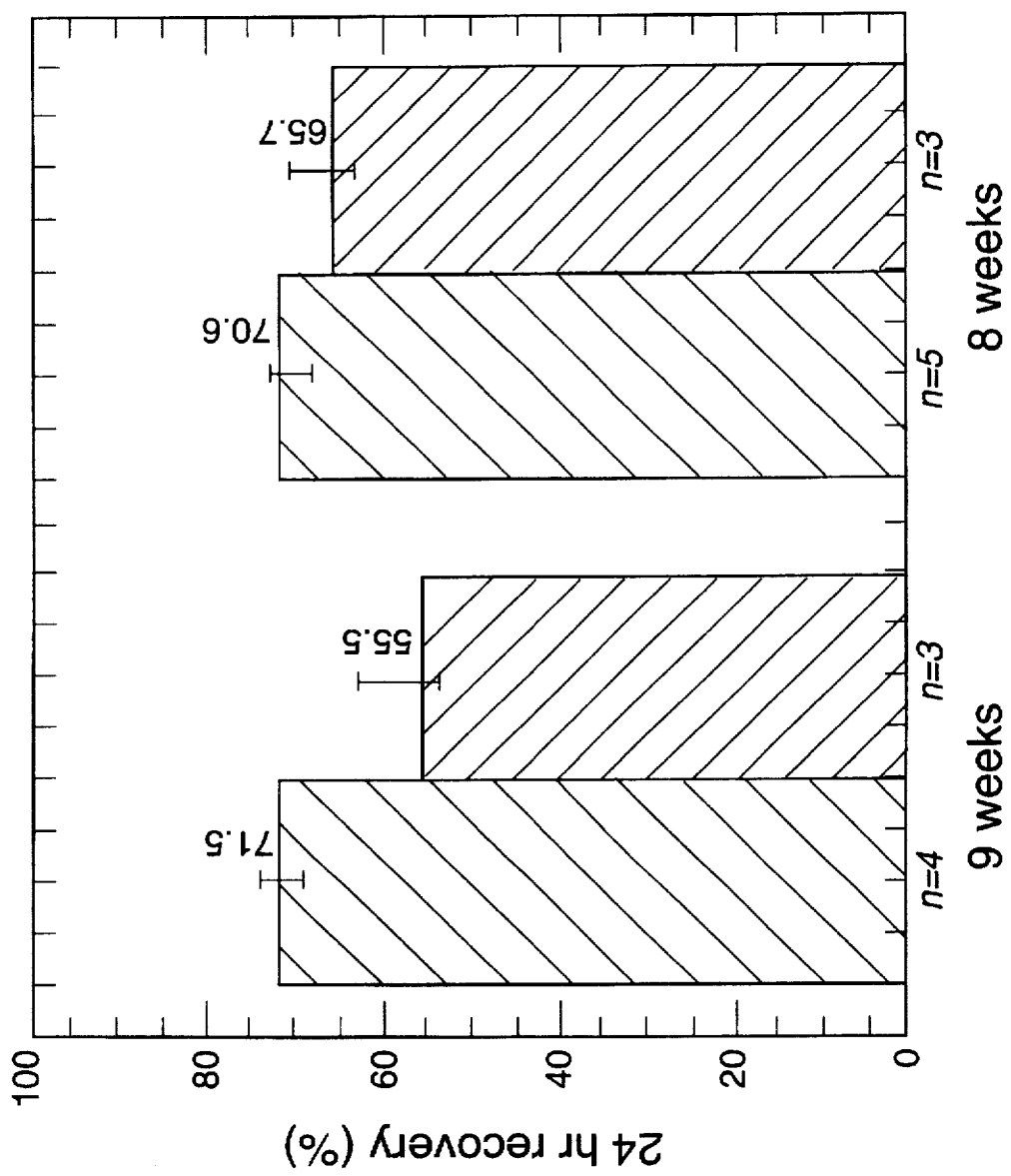
FIGS. 1a and 1b show in vivo recovery for red blood cells aerobically (right-sloping hatching) and anaerobically (left-sloping hatching) stored for 8 and 9 weeks in OFAS1 (about 2 mM of adenine, about 110 mM of dextrose, about 65 mM of mannitol, about 20 mM of sodium citrate, and about 20 mM of sodium dihydrogen phosphate, in water).

Briefly, the present invention includes improvement of the in vivo survival characteristics of transfused red blood cells (RBCs) that have been stored at 4° C. for prolonged periods of time by removing oxygen therefrom at the time of storage, adding a preservation solution, OFAS1, which consists essentially of an aqueous solution of adenine, dextrose, mannitol, citrate ion, and dihydrogen phosphate ion in place of conventional storage solutions, and preventing any further exposure of the stored RBCs to oxygen. The in vitro diagnostics of hemolysis, vesicle production and ATP levels, when taken together, provide a useful indication of in vivo survival. Additionally, evidence for the synergism of anaerobic storage and the use of OFAS1 was obtained from these in vitro diagnostic measurements. The beneficial effects of oxygen removal during refrigerated storage of red blood cells in OFAS1 additive solution were further investigated by in vivo recovery measurements in humans. These measurements completely support the in vitro conclusions. The OFAS1 additive solution contains ingredients that are found in the FDA approved solutions AS-1 (2 mM of adenine, 122 mM of dextrose, 42 mM of mannitol, and 154 mM of sodium chloride as currently formulated), and AS-3 (2.2 mM of adenine, 61 mM of dextrose, 70 mM of sodium chloride, 20 mM of sodium citrate, 2 mM of citric acid, and 20 mM of sodium hydrogen phosphate, as currently formulated), and does not incorporate any new ingredients. The OFAS1 solution does not contain sodium chloride, however. The pH of the OFAS1 solution was adjusted to approximately 7.1 with the addition of sodium hydroxide. Clearly, other bases can be used to accomplish this purpose. The solution was then sterilized by filtration through 0.2 µm pore filters, since it was believed that deterioration would occur if the additive solution was sterilized according to the generally used procedure of autoclaving.

Oxygen removal, and the effects of the OFAS1 additive solutions were investigated with red blood cells stored in standard polyvinyl chloride (PVC) blood bags with di-(2-ethylhexyl) phthalate (DEHP) plasticizer. Oxygen was removed from warm RBCs by flushing the blood bags with argon between 6 and 10 times, which reduced the oxygen level of the RBCs to below 10% of the level of oxygen when obtained (each transfer bag containing the red cells was filled with purified Ar and shaken gently for approximately 10 min. before expelling the gas). For red blood cells prepared for in vitro diagnostics a unit of blood was typically stored in AS-1/AS-3 additive solution in a standard storage bag for between 2 and 5 days after collection at a blood bank. Each unit of blood was then subdivided into about 120 mL aliquots, placed in DEHP plasticized PVC transfer bags with 150 mL capacity, and stored at 4° C. in a light-shielded blood bank refrigerator. No measurements were performed with red blood cells which were not shielded from the light; however, it is believed by the present inventors that fluorescent light does not cause significant red blood cell deterioration. Samples were withdrawn as needed via a sterile septum sampling port. Rapid cooling after rapid purging is essential to prevent lactic acid buildup in the RBCs. Moreover, it should be mentioned that the oxygen can also be removed after the RBCs are cooled. However, since the RBCs are unprotected from the effects of oxidation once cooled, and since oxygen removal is more rapid at 37° C. or 21° C. when compared with 4° C., the preferred procedure is to cool them after oxygen removal. As reported by Hogman et al., supra, conventional PVC blood storage bags are permeable to $O_2$. It takes about 4 weeks of conventional storage for a unit of packed red blood cells to become fully oxygenated. In order to evaluate the long-term effects of replacing the storage gas, transfer bags were stored in an anaerobic chamber filled with an inert gas such as argon. Blood bag gas exchange was further enhanced by 2–3 cycles of exposing the anaerobic chamber to partial vacuum followed by filling with the chosen inert gas. In addition, about 10% (v/v) of hydrogen gas was added to the argon storage gas along with a palladium catalyst in the anaerobic chamber that houses the stored blood to continuously remove traces of $O_2$ emerging from the blood bags.

For "control" samples, cells were stored in the 150 ml transfer packs without further treatment. For both aerobic and anaerobic storage in OFAS1, cells were centrifuged at 2,000x g in the transfer pack, and the supernatant was removed and replaced with an appropriate amount of the additive solution to achieve a final hematocrit (Hct) of about 40. Membrane vesicle production was quantified by measuring the protein content of isolated vesicle fractions. The ATP concentration was measured with a commercial diagnostic kit. All data are given as the average value obtained from 4–6 units of blood.

In vivo tests were conducted using a cohort of 10 subjects divided into two groups. A unit of blood was first collected into CP2D anticoagulant solution. Subsequently, platelets and plasma were removed and OFAS1 added. Oxygen was then removed as described hereinabove. Whole blood units were stored undisturbed in the OFAS1 additive solution under both anaerobic and aerobic conditions for 8 and 9 weeks. The 24 h post-transfusion recovery was determined using the well-known Tc-99m/Cr-51 double labeling protocol. The results of the 24 h in vivo recovery experiments are shown in the Table.

TABLE

| SUBJECT | ANAEROBIC Cr-51/Tc-99 m | Cr-51 | AEROBIC Cr-51/Tc-99 m | Cr-51 |
|---|---|---|---|---|
| 9 wk A | 73.4 | 80.3 | 62.3 | 68.3 |
| 9 wk B | 71.6 | 80.0 | 47.7 | 60.3 |
| 9 wk C | 67.4 | 72.6 | | |
| 9 wk D | 73.4 | 80.9 | 56.5 | 63.5 |
| 8 wk E | 71.4 | 79.1 | 60.2 | 68.4 |
| 8 wk F | 70.7 | 77.1 | 69.7 | 76.6 |
| 8 wk G | 74.1 | 83.7 | | 77.8 |
| 8 wk H | 68.6 | 81.5 | 67.1 | 70.0 |
| 8 wk I | 68.2 | 74.8 | | |
| 9 wk average | 71.5 | 78.5 | 55.5 | 64.0 |
| 9 wk std. Dev. | 2.8 | 3.9 | 7.4 | 4.0 |
| 8 wk average | 70.6 | 79.2 | 65.7 | 73.2 |
| 8 wk std. Dev. | 2.4 | 3.5 | 4.9 | 4.7 |

Figure 1B:
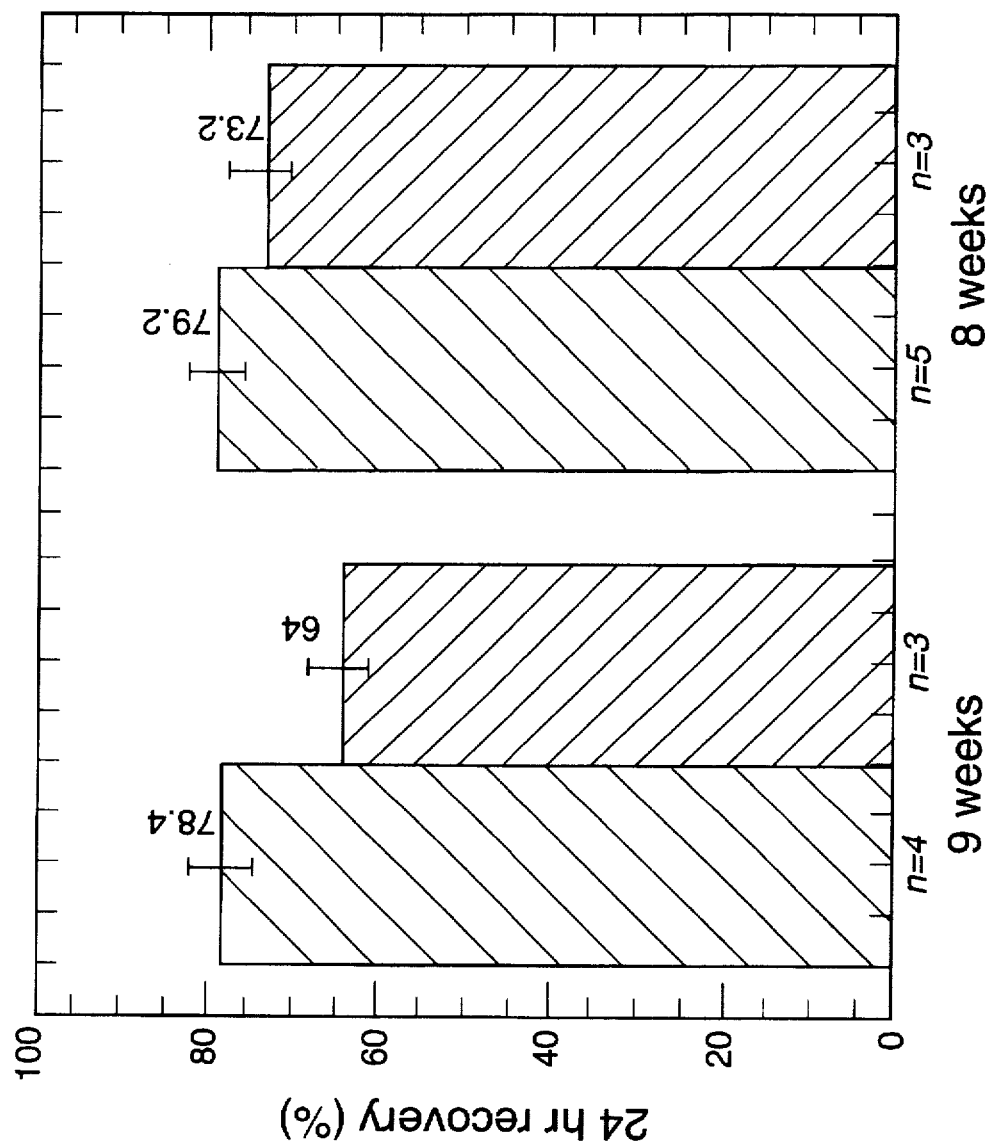

Reference will now be made in detail to the preferred embodiments of the present invention, examples of which are illustrated in the accompanying drawings. Turning now to the FIGS., FIG. 1a shows the results derived from the Cr-51 and Tc-99m double-labeling procedures, while FIG. 1b shows results derived from Cr-51 data only. Red blood cells were stored in OFAS1 with a Hct of about 40% (obtained using a hematocrit centrifuge), with oxygen removal (left-sloping hatching) and without oxygen removal (right-sloping hatching). Current practice in the blood storage industry is to store red blood cells with a hematocrit of about 60% (40% by volume of storage solution and 60% by volume of packed red cells). In the present invention, hematocrits of between 30% and 60% are expected to give acceptable storage characteristics; however, with a Hct of less than 40%, the volume of the storage bags begins to become large.

The number, n, designates the number of subjects averaged. For one subject in the 8 week aerobic sample, a Tc-99m label was not available; therefore, only single labeling data were obtained for that individual. Due to a number of drop-outs, averages of fewer than 5 subjects were included in the results presented. The following conclusions may be derived from the Table and from FIGS. 1a and 1b:

1. Oxygen removal enhances the 24 h recovery by 16% after 9 weeks of storage;
2. As expected, the recovery rates for the single label are considerably higher than those for the double label procedure in all cases (by 7–9%);
3. Virtually no change in the rate of 24 h recovery was seen between 8 and 9 weeks of anaerobic storage, in contrast to an 10% drop in recovery for samples stored in the presence of oxygen; and
4. The smaller cohorts (4 subjects instead of 5) in the anaerobic trial did not have increased subject-to-subject variability both at 8 and 9 weeks of storage.

Figure 3:
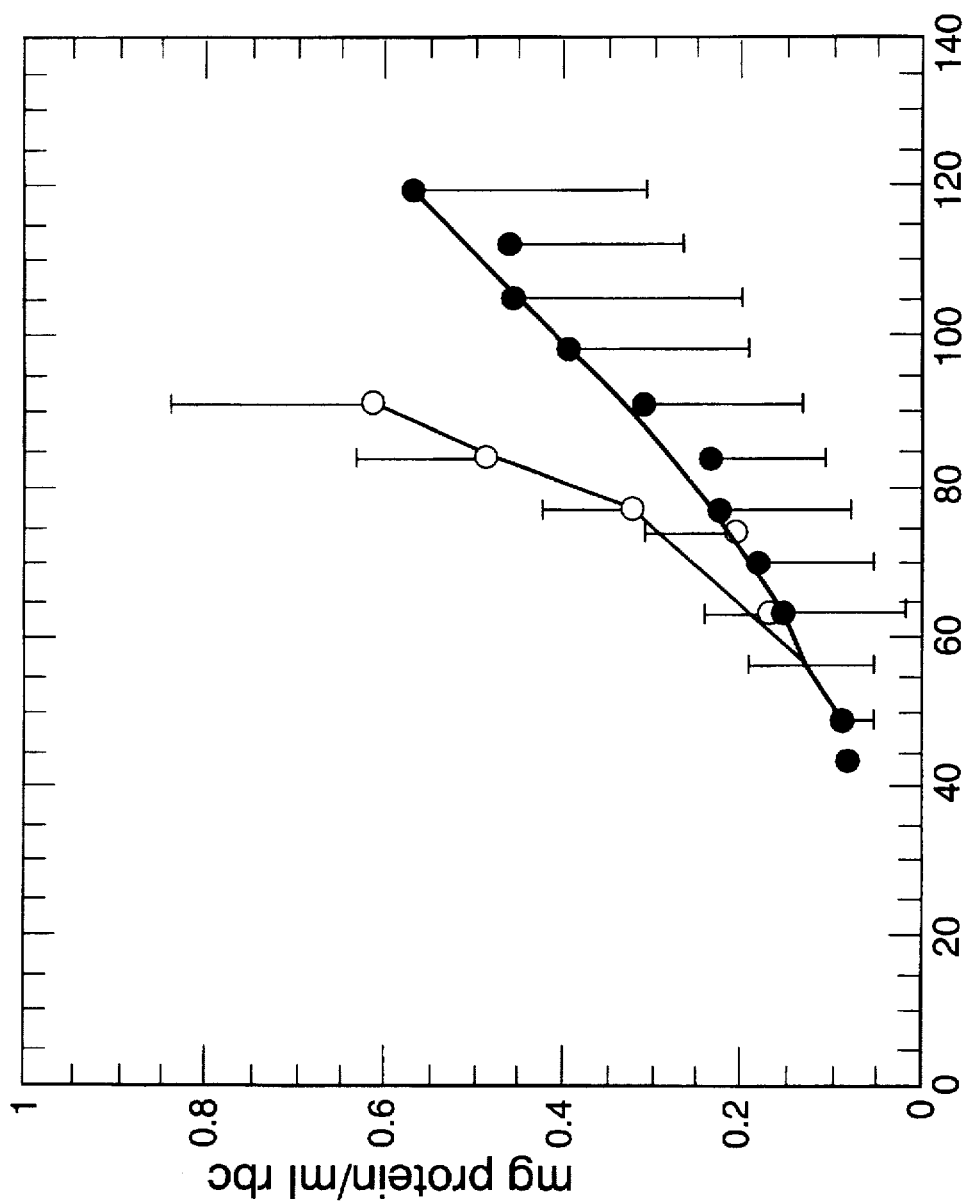
FIG. 3 shows vesicle production for red blood cells, for which in vivo measurements were made, as a function of time, where the cells were aerobically (open circles) and anaerobically (black circles) stored in OFAS1.
Figure 4:
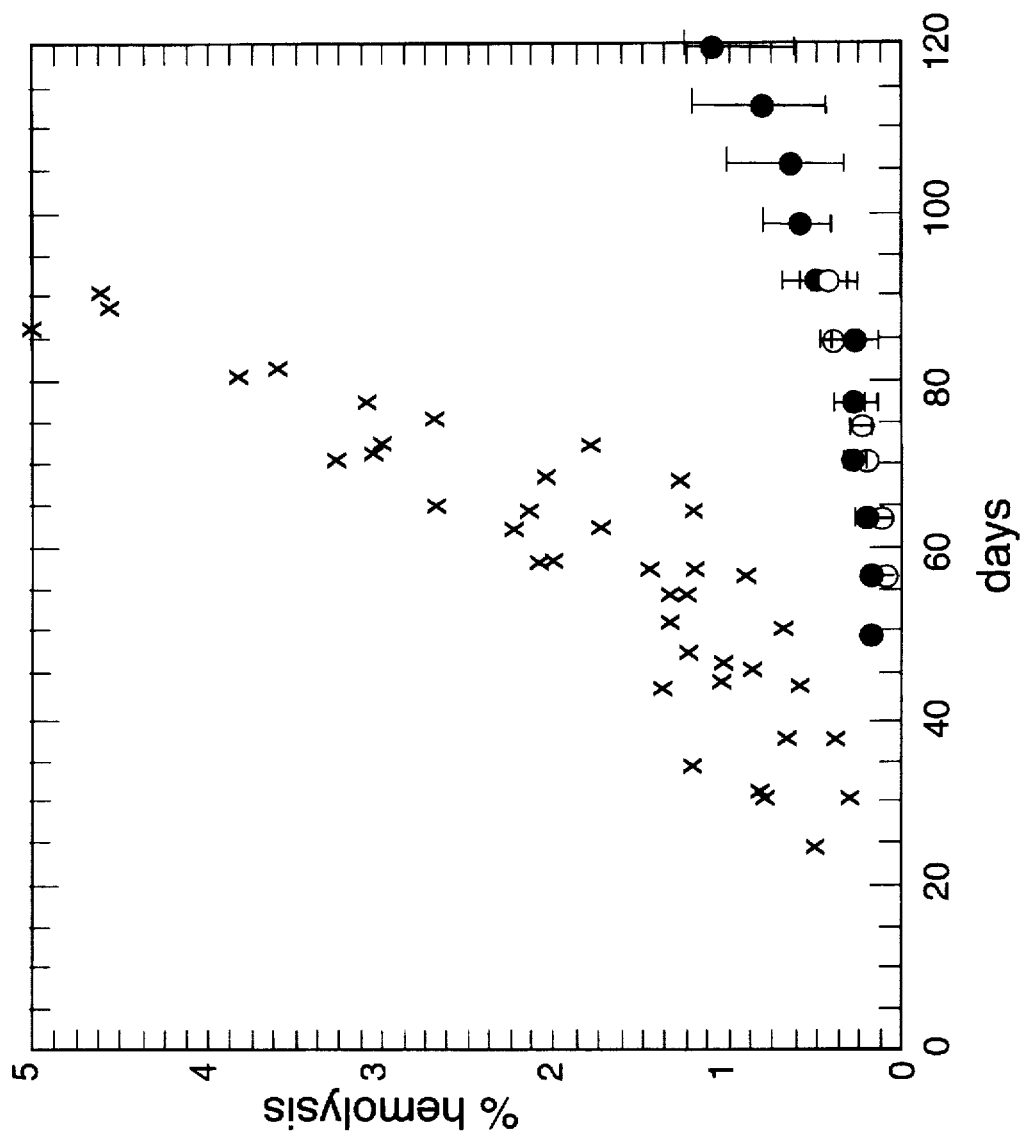
FIG. 4 shows hemolysis of red blood cells for which in vivo measurements were made, as a function of time, where the cells were stored aerobically (open circles) and anaerobically (black circles) in OFAS1. Shown also are data from aerobically stored cells in conventional storage media (Xs).

After conducting the above-described 24 h in vivo recovery studies, the red blood cell samples were stored for an additional 4–8 weeks beyond the infusion date. Several in vitro diagnostic tests (including ATP levels, vesicle production and the extent of hemolysis) were carried out for these samples, the results of which are shown in FIGS. 2–4. Unlike for blood used solely for in vitro investigations, samples were taken weekly from the original storage bag, and ATP levels were determined beginning after 8 or 9 weeks of storage. All data obtained from blood prepared for the in vivo experiments were averaged, and the standard deviations are shown in the FIGS.

Figure 2A:
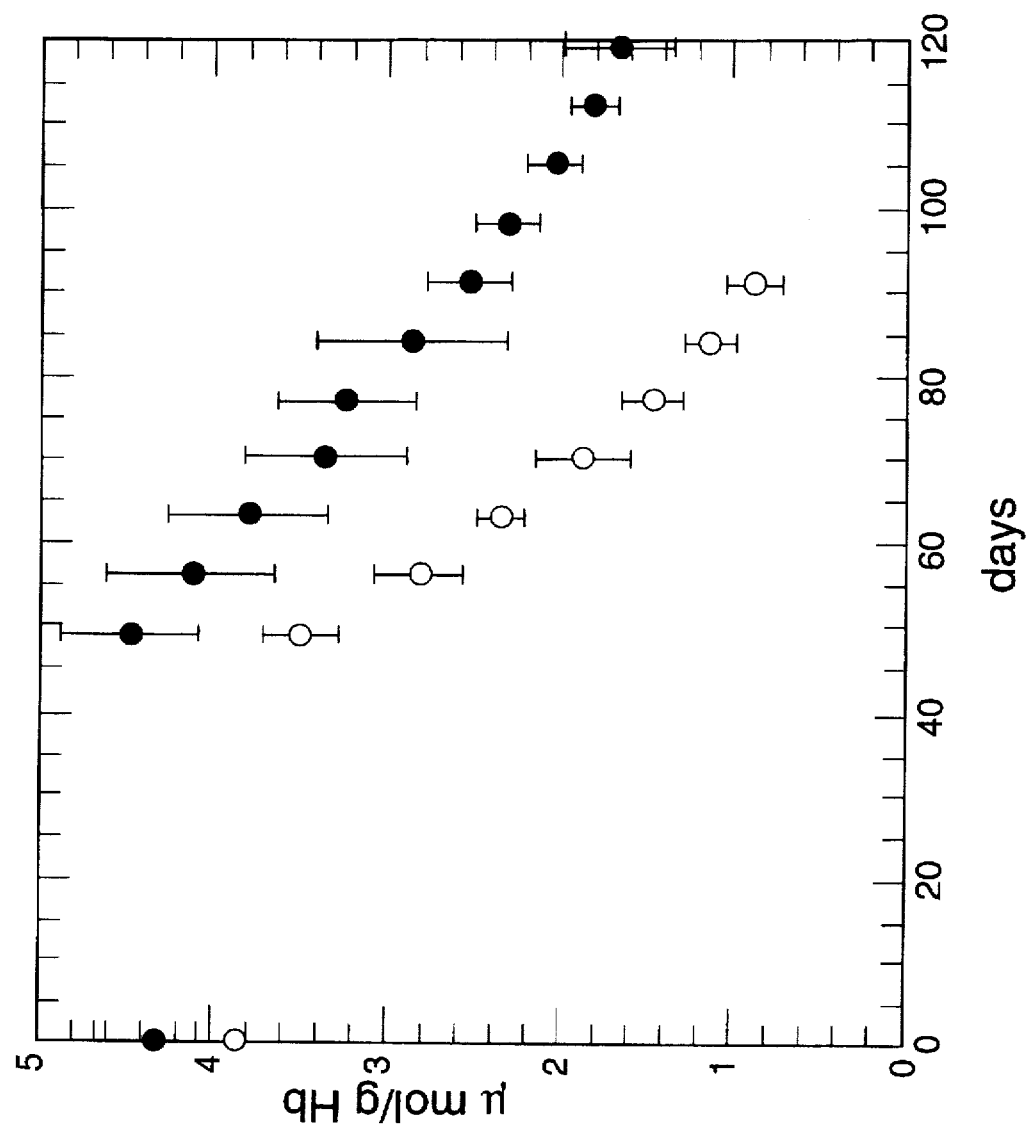
FIGS. 2a, 2b, and 2c show the levels of adenosine triphosphate (ATP) in red blood cells, for which in vivo recovery measurements were made, as a function of time.
Figure 2B:
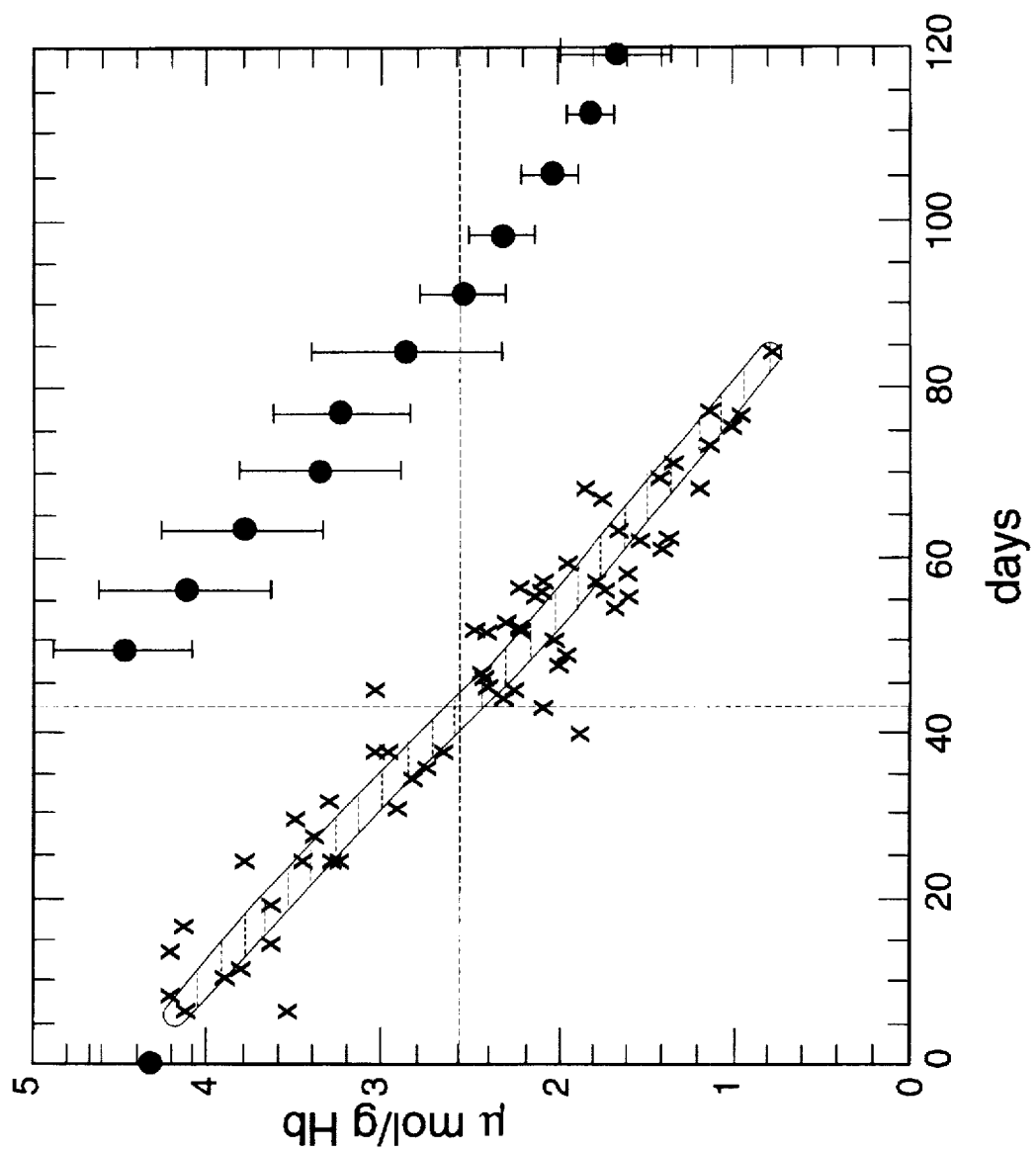
Figure 2C:
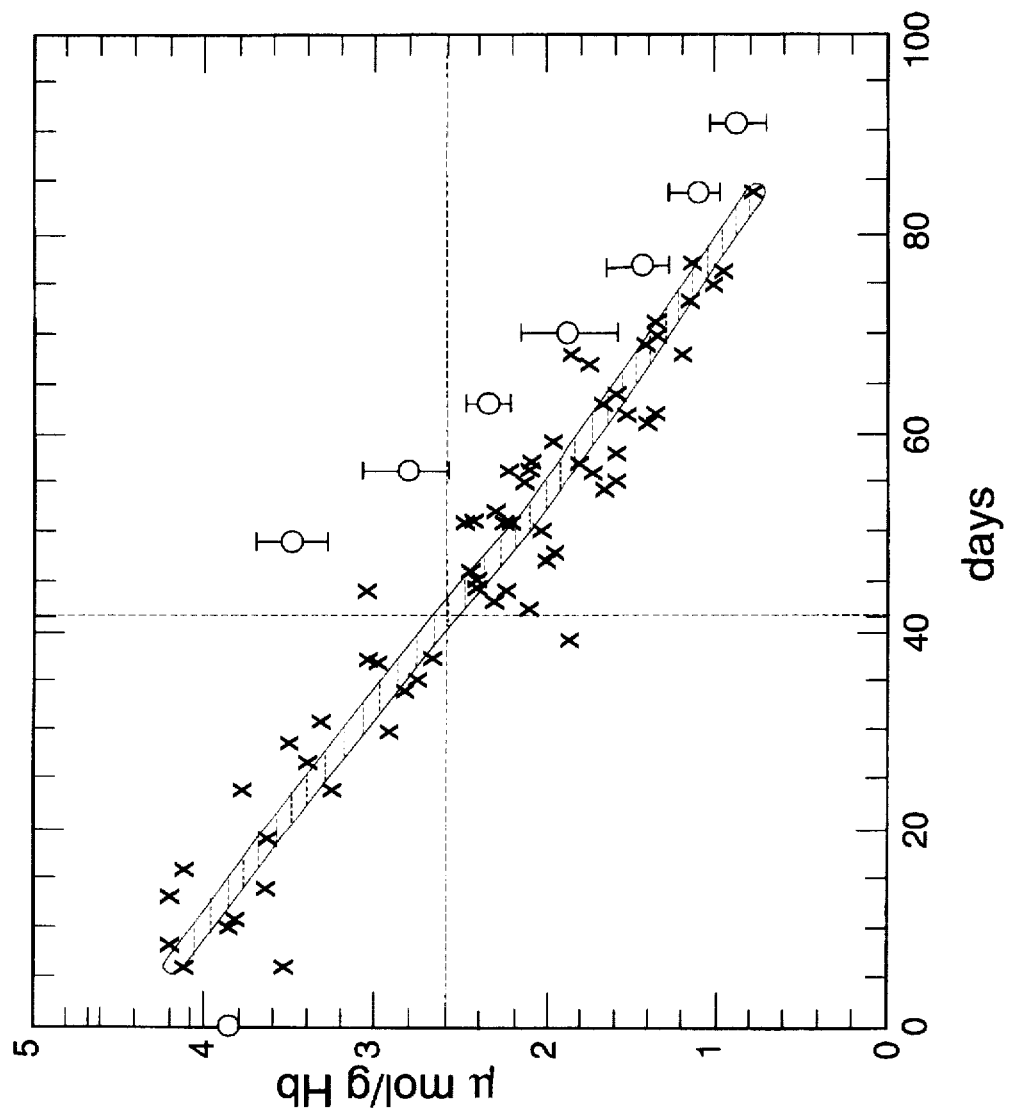

FIG. 2a compares cellular ATP levels as a function of time for aerobically (open circles) and anaerobically stored (black circles) cells in OFAS1. FIG. 2b is a comparison of ATP levels between red blood cells stored anaerobically in OFAS1 (black circles) and "control" red cells stored aerobically in AS1/AS3 (Xs), and FIG. 2c is a comparison of ATP levels between cells stored aerobically in OFAS1 (open circles) with the "control" red cells stored aerobically in AS1/AS3 (Xs) as a function of time. The dotted lines indicate the 6 week storage point and the ATP level of conventionally stored red cells. For red cells anaerobically stored in OFAS1, comparable levels of ATP were reached after 13 weeks of storage. For the in vitro control experiments, each data point represents an average of 4–7 red blood cell samples aerobically stored in AS-1 and AS-3, as described hereinabove. These data were gathered from over 120 units of stored red cells over a two-year period. FIG. 2c is a comparison of ATP levels between conventional ("control") aerobic storage (Xs) and aerobic storage in OFAS1 (open circles). It is seen that red blood cells aerobically stored in OFAS1 show significant elevation of ATP levels when compared to cells aerobically stored in AS-1/AS-3 at 7 weeks. However, the decline of ATP levels over time was more rapid than for samples stored in OFAS1, and approached the levels of conventional additive solutions beyond 10 weeks.

FIG. 3 shows vesicle production for red cells on which in vivo measurements were made as a function of time. The amount of vesicle isolated from the cell suspensions was evaluated using standard protein assay techniques. All data were averaged and the standard deviations are shown in FIG. 3. Anaerobic storage in OFAS1 is represented by the black circles, while aerobic storage in OFAS1 is represented by the open circles.

FIG. 4 shows the hemolysis of red cells for which in vivo measurements were made as a function of time. The extent of hemolysis was determined according to standard procedures. All data obtained from blood prepared for the in vivo experiments were averaged, and the standard deviations are shown in the FIG. Hemolysis control data from aerobic storage in AS-1/AS-3 ("control") are also shown for comparison. The extent of hemolysis for the aerobic AS1/AS3 control (Xs) was found to be significantly higher than for the aerobically stored in vivo samples in OFAS1 (open circles) and the anaerobically stored cells in OFAS1 (black circles). It is currently believed by the present inventors that the observed increase in hemolysis rates of the control samples resulted from more frequent thorough mixing to which these samples were subjected during weekly sampling processes. By contrast, the in vivo samples were only inverted gently once per week, until the date of infusion.

From the in vitro results, it may be concluded that:
1. ATP levels are significantly higher with anaerobic storage than with aerobic storage in OFAS1 (FIG. 2a);
2. The reduced levels of ATP found for aerobic controls (aerobic in vitro data at 6 weeks) are approached only after 90 days of storage in the absence of oxygen (FIG. 2b);
3. Higher ATP levels were observed with aerobic samples that were stored in OFAS1 when compared to conventional AS-1 and AS-3 controls. These data indicate a modest benefit of OFAS1 in elevating ATP levels, even under aerobic storage. However, the higher ATP level did not directly enhance the 24 h recovery rate after 8 weeks of storage (FIG. 2c);
4. Rates of vesicle production are similar at 8 and 9 weeks between the two forms of storage. However, vesicle production accelerates beyond 10 weeks in the aerobic samples (FIG. 3); and
5. Rates of hemolysis are similar for aerobic and anaerobic samples for up to 11 weeks of refrigerated storage (FIG. 4). Control in vitro measurements show considerably higher hemolysis rates in aerobically stored samples. As mentioned, this may be partly due to the handling needed to thoroughly mix the bag for weekly sampling (that is, the extra handling for sampling between weeks 0 and 9, compared with the in vivo samples). Such handling did not appear to adversely impact the blood stored anaerobically (data not shown). It may be that the OFAS1 also contributes to a reduction in hemolysis rates, but no data is currently available concerning this point.

Figure 5:
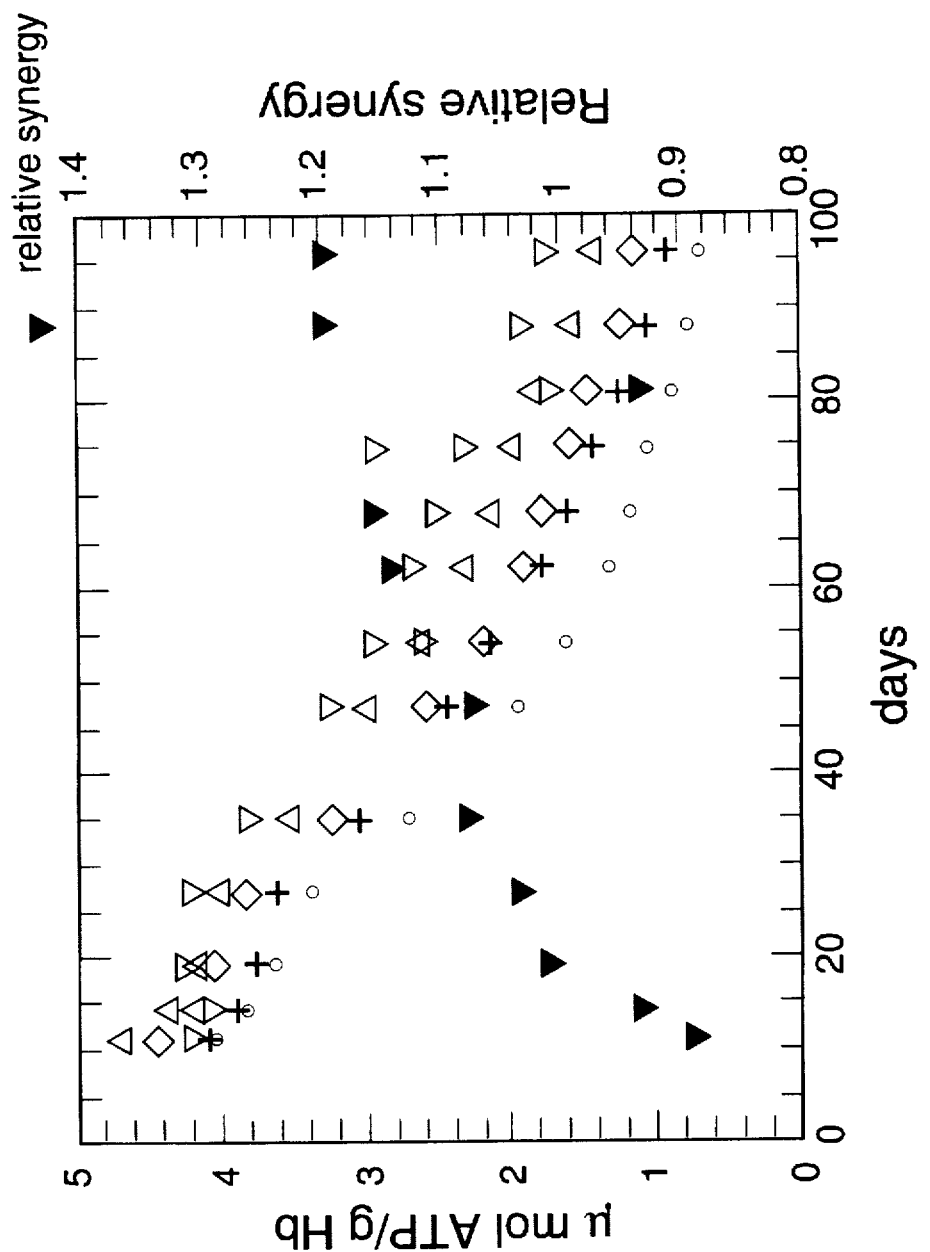
FIG. 5 shows a comparison of the level of ATP as a function of time among red blood cells stored aerobically in conventional storage media (small circles), cells stored anaerobically in conventional storage media (diamonds), cells stored aerobically in OFAS1 (pluses), and cells stored anaerobically in OFAS1 (inverted open triangles), and shows the synergistic effect of anaerobic storage in OFAS1. None of the red blood cells used in FIG. 5 were used for in vivo measurements.

FIG. 5 shows a comparison of the level of ATP as a function of time among red blood cells stored aerobically in conventional storage media (small circles), cells stored anaerobically in conventional storage media (diamonds), cells stored aerobically in OFAS1 (pluses), and cells stored anaerobically in OFAS1 (inverted open triangles), and shows the synergistic effect of anaerobic storage in OFAS1. None of the red blood cells used in FIG. 5 were used for in vivo measurements. If one defines "synergy" as being equal to μmol of ATP per gram of hemoglobin for anaerobic storage of the red cells in OFAS1 divided by the sum of μmol of ATP per gram of hemoglobin for cells aerobically stored in AS-1 (control), plus the difference in μmol of ATP per gram of hemoglobin between the control and that for cells aerobically stored in OFAS1, plus the difference in μmol of ATP per gram of hemoglobin between the control and that for is cells anaerobically stored in AS-1 (the sum being plotted as upright hollow triangles), one observes the synergistic effect of aerobically storing the cells OFAS1 plotted as inverted black triangles in FIG. 5.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for storing red blood cells which comprises the steps of:
   a. mixing a sample of whole blood containing the red blood cells to be stored with an anticoagulant solution, forming thereby a first suspension of red blood cells;
   b. concentrating the red blood cells from the liquid portion of the first suspension, forming thereby a mass of packed red blood cells;
   c. mixing the packed red blood cells so produced with an additive solution which consists essentially of a solution of adenine, dextrose, mannitol, citrate ion, and dihydrogen phosphate ion, in water, forming thereby a second suspension of red blood cells;
   d. reducing the oxygen level of the red blood cells in the second suspension of red blood cells to approximately 10% or less of the level of oxygen in the whole blood by flushing the red blood cells with an inert gas; and
   e. storing the red blood cells in the second suspension of red blood cells at 4° C.

2. The method for storing red blood cells as described in claim 1, further comprising the step of storing the second suspension of red blood cells in an oxygen-permeable container which is located in an oxygen-free environment.

3. The method for storing red blood cells as described in claim 1, further comprising the step of storing the second suspension of red blood cells in an oxygen-permeable container which is located in an oxygen-free environment containing oxygen scavenging materials.

4. The method for storing red blood cells as described in claim 1, wherein said step of reducing the level of oxygen of the red blood cells in the second suspension takes place before said step of cooling the second suspension to 4° C.

5. The method for storing red blood cells as described in claim 1, wherein the additive solution consists essentially of a solution of about 2 mM of adenine, about 110 mM of dextrose, about 65 mM of mannitol, about 20 mM of sodium citrate, and about 20 mM of sodium dihydrogen phosphate, in water.

6. The method for storing red blood cells as described in claim 1, wherein the amount of additive solution is chosen to be sufficient to achieve a final hematocrit of between 30% and 60%.

7. The method for storing red blood cells as described in claim 1, wherein the pH of the additive solution is adjusted to be approximately 7.1.

8. A method for storing red blood cells which comprises the steps of:
   a. forming a mass of packed red blood cells;
   b. mixing the packed red blood cells with an additive solution which consists essentially of a solution of adenine, dextrose, mannitol, citrate ion, and dihydrogen phosphate ion, in water, forming thereby a suspension of red blood cells;
   c. reducing the level of oxygen in the suspension of red blood cells to approximately 10% or less of the level of oxygen in the mass of packed red blood cells by flushing the red blood cells with an inert gas; and
   d. storing the red blood cells in the suspension of red blood cells at 4° C.

9. The method for storing red blood cells as described in claim 8, further comprising the step of storing the suspension of red blood cells in an oxygen-permeable container which is located in an oxygen-free environment.

10. The method for storing red blood cells as described in claim 8, further comprising the step of storing the suspension of red blood cells in an oxygen-permeable container which is located in an oxygen-free environment containing oxygen scavenging materials.

11. The method for storing red blood cells as described in claim 8, wherein said step of reducing the level of oxygen in the red blood cells in the suspension takes place before said step of cooling the suspension to 4° C.

12. The method for storing red blood cells as described in claim 8, wherein the additive solution consists essentially of about 2 mM of adenine, about 110 mM of dextrose, about 65 mM of mannitol, about 20 mM of sodium citrate, and about 20 mM of sodium dihydrogen phosphate, in water.

13. The method for storing red blood cells as described in claim 8, wherein the amount of additive solution is chosen to be sufficient to achieve a final hematocryte of between 30 and 60%.

14. The method for storing red blood cells as described in claim 8, wherein the pH of the additive solution is adjusted to be approximately 7.1.

15. A method for storing red blood cells which comprises the steps of:
   a. forming a mass of packed red blood cells;
   b. mixing the packed red blood cells with an additive solution comprising adenine, dextrose, mannitol, citrate ion, and dihydrogen phosphate ion, with no sodium chloride, dissolved in water, forming thereby a suspension of red blood cells;
   c. reducing the level of oxygen in the suspension of red blood cells to approximately 10% or less of the level of oxygen in the mass of packed red blood cells by flushing the red blood cells with an inert gas; and
   d. storing the red blood cells in the suspension of red blood cells at 40° C.

16. The method for storing red blood cells as described in claim 15, further comprising the step of storing the suspension of red blood cells in an oxygen-permeable container which is located in an oxygen-free environment.

17. The method for storing red blood cells as described in claim 15, further comprising the step of storing the suspension of red blood cells in an oxygen-permeable container which is located in an oxygen-free environment containing oxygen scavenging materials.

18. The method for storing red blood cells as described in claim 15, wherein said step of reducing the level of oxygen in the red blood cells in the suspension takes place before said step of cooling the suspension to 4° C.

19. The method for storing red blood cells as described in claim 15, wherein the additive solution comprises about 2 mM of adenine, about 110 mM of dextrose, about 65 mM of mannitol, about 20 mM of sodium citrate, and about 20 mM of sodium dihydrogen phosphate, with no sodium chloride, dissolved in water.

20. The method for storing red blood cells as described in claim 15, wherein the amount of additive solution is chosen to be sufficient to achieve a final hematocrit of between 30% and 60%.

21. The method for storing red blood cells as described in claim 15, wherein the pH of the additive solution is adjusted to be approximately 7.1.

* * * * *